(12) United States Patent
Murphy et al.

(10) Patent No.: US 10,159,606 B2
(45) Date of Patent: Dec. 25, 2018

(54) TWO-LAYER COMPRESSION BANDAGE SYSTEM AND METHODS OF MAKING AND USING THE SAME

(75) Inventors: Thomas S. Murphy, Boxford, MA (US); Fred A. Cronin, Exeter, NH (US)

(73) Assignee: Andover Healthcare, Inc., Salisbury, MA (US)

(*) Notice: Subject to any disclaimer, the term of this patent is extended or adjusted under 35 U.S.C. 154(b) by 0 days.

(21) Appl. No.: 13/410,439

(22) Filed: Mar. 2, 2012

(65) Prior Publication Data

US 2012/0238933 A1  Sep. 20, 2012

Related U.S. Application Data

(60) Provisional application No. 61/452,455, filed on Mar. 14, 2011.

(51) Int. Cl.
*A61F 13/02* (2006.01)
*A61F 17/00* (2006.01)
*A61F 13/00* (2006.01)
*A61F 13/08* (2006.01)

(52) U.S. Cl.
CPC .... *A61F 13/0273* (2013.01); *A61F 13/00987* (2013.01); *A61F 13/08* (2013.01); *A61F 13/085* (2013.01); *A61F 17/00* (2013.01)

(58) Field of Classification Search
CPC .... A61F 5/00; A61F 13/00; A61F 5/40; A61F 2013/00089; A61F 2013/00119; A61F 2013/00174; A61F 13/0273; A61F 13/00987; A61F 13/08; A61F 13/085
USPC ............... 602/43, 46, 48, 75, 74, 79, 60–62
See application file for complete search history.

(56) References Cited

U.S. PATENT DOCUMENTS 2,687,723 A * 8/1954 Stern .................... A61F 13/085
602/75
3,536,072 A * 10/1970 Quello ........................... 602/23
3,566,871 A * 3/1971 Richter ................ A61L 15/425
604/362

(Continued)

FOREIGN PATENT DOCUMENTS

EP  1709947  10/2006
FR  1111157  2/1956

(Continued)

OTHER PUBLICATIONS

D.D.I. Wright et al., "The Function of Multiple Layer Compression Bandaging in the Management of Venous Ulcers," Swiss Med., vol. 10, No. 4a, pp. 109-110 (1988).

(Continued)

*Primary Examiner* — Kari Rodriquez
*Assistant Examiner* — Camtu Nguyen
(74) *Attorney, Agent, or Firm* — McLane Middleton, Professional Association (57) ABSTRACT

A compression kit including an inner layer, comprising a foam material, and an outer layer, comprising a separate elastic compression bandage is disclosed. An article comprising foam with two major surfaces, one of which has been coated with a hydrophilic agent to be applied against the skin is disclosed. A method of manufacturing the foam article with the skin-facing hydrophilic surface is disclosed. A method of applying the compression kit to a patient's leg or other body part is disclosed.

26 Claims, 6 Drawing Sheets

(56) References Cited

U.S. PATENT DOCUMENTS

| | | | |
|---|---|---|---|
| 4,377,160 A * | 3/1983 | Romaine | 602/2 |
| 4,424,808 A * | 1/1984 | Schafer et al. | 602/76 |
| 4,517,968 A * | 5/1985 | Greene et al. | 602/27 |
| 4,634,626 A * | 1/1987 | Yamaguchi et al. | 428/312.4 |
| 4,661,099 A * | 4/1987 | von Bittera et al. | 604/290 |
| 4,887,368 A * | 12/1989 | Latzke | 607/111 |
| 4,977,892 A * | 12/1990 | Ewall | A61F 13/023 523/105 |
| 5,203,764 A * | 4/1993 | Libbey et al. | 602/5 |
| 5,762,623 A | 6/1998 | Murphy et al. | |
| 6,156,424 A | 12/2000 | Taylor | |
| 7,175,897 B2 * | 2/2007 | Baron | A61B 5/14532 428/343 |
| 7,713,222 B2 * | 5/2010 | Evans et al. | 602/8 |
| 8,002,721 B2 * | 8/2011 | Bretl et al. | 602/2 |
| 8,491,514 B2 * | 7/2013 | Creighton | A61F 13/10 602/60 |
| 8,779,230 B2 | 7/2014 | Murphy et al. | |
| 2005/0136238 A1 * | 6/2005 | Lindsay | A47L 13/16 428/304.4 |
| 2005/0158539 A1 | 7/2005 | Murphy et al. | |
| 2006/0073328 A1 | 4/2006 | Murphy et al. | |
| 2006/0229544 A1 * | 10/2006 | Schuren | A61F 13/069 602/53 |
| 2007/0259163 A1 | 11/2007 | Connolly et al. | |
| 2007/0299383 A1 | 12/2007 | Murphy et al. | |
| 2008/0014386 A1 | 1/2008 | Murphy et al. | |
| 2008/0014387 A1 | 1/2008 | Murphy et al. | |
| 2008/0031931 A1 | 2/2008 | Gunn | |
| 2008/0114278 A1 * | 5/2008 | Fabo | A61F 13/023 602/48 |
| 2009/0075042 A1 | 3/2009 | Murphy | |
| 2009/0112141 A1 | 4/2009 | Derr | |
| 2009/0112144 A1 | 4/2009 | Boyer | |
| 2010/0055157 A1 | 3/2010 | Gunn | |
| 2010/0286298 A1 * | 11/2010 | Casati | C08G 18/4829 521/159 |
| 2011/0060277 A1 * | 3/2011 | Lilley | A61B 17/00491 604/104 |
| 2012/0238933 A1 | 9/2012 | Murphy et al. | |
| 2016/0166440 A1 | 6/2016 | El-Tahlawy et al. | |
| 2017/0203541 A1 | 7/2017 | El-Tahlawy et al. | |

FOREIGN PATENT DOCUMENTS

| | | | |
|---|---|---|---|
| GB | 718040 | * | 1/1954 |
| GB | 718040 | | 11/1954 |

OTHER PUBLICATIONS

Extended European Search Report dated Feb. 11, 2014, received in EP12159127.5.

European Search Report dated Mar. 10, 2017, received in EP12159127.5.

* cited by examiner

TWO-LAYER COMPRESSION BANDAGE SYSTEM AND METHODS OF MAKING AND USING THE SAME

CROSS-REFERENCE TO RELATED APPLICATION(S)

This application claims priority to U.S. Provisional Application No. 61/452,455, filed Mar. 14, 2011. The aforementioned application is incorporated herein by reference in its entirety.

BACKGROUND

Compression bandages are frequently used in medical and sports applications requiring a strong and reliable, yet comfortable and easily applied, means of securing a limb or other body segment for prolonged periods of time. For example, strains and sprains can cause inflammation and the accompanying accumulation of fluid around a sprained joint. Wrapping the affected joint securely with an elastic bandage can prevent excess fluid from accumulating and causing additional tissue damage.

In addition, chronic venous disease, including valve insufficiency and venous wall damage, and leg ulcers of various origins, including venous stasis ulcers, arterial (ischemic) ulcers and neurotrophic ulcers, are common medical problems. Leg ulcers are wounds or open sores that do not heal, or otherwise recur repeatedly, and cause persistent swelling as well as burning, itching, irritation and discoloration of the skin. Treatment of leg ulcers generally includes compression in addition to topical protection of the wound and antimicrobial treatment of the affected area.

Therapeutic compressive pressures are based on the principle that extra-vascular pressure should equal excess venous pressure in order to restore normal venous flow from the extremities back to the torso, e.g., from the foot to the thigh. Stress on the venous system is already the greatest in the leg in standing position because the veins must move blood against the force of gravity. Ideal leg compression mirrors the leg's natural degressive pressure gradient, i.e., higher pressure at the ankle and lower pressure at the thigh, which results from the gradual increase of leg diameter from the ankle to the thigh. Thus, therapeutic compressive pressure goals vary from patient to patient and at different locations in each patient's leg based on venous pressure measurements.

Traditionally, compression therapy for leg ulcers has involved wrapping a patient's leg with a layer of cotton batting followed by a compression bandage or sleeve. Better results are now achieved with the application of a 3 to 4 layer bandage system, by which different types of bandages are combined to achieve and sustain a suitable therapeutic sub-bandage compressive pressure. A common example is the four-layer system described in "The Function of Multiple Layer Compression Bandaging in the Management of Venous Ulcers," D D I Wright et al., SWM, 10, 109-10 (1988). The four layers include (1) a skin-facing layer of cotton wool, (2) a lightweight bandage, (3) a light compression bandage, and (4) a flexible cohesive bandage.

Despite their potential to deliver therapeutic compressive pressure, the process of applying such 3 to 4 layer bandage systems is time intensive, which reduces patient compliance. Also, the bandages in these systems often require pleats or tucks in order to conform to the patient's leg and may slip or wrinkle following application, all of which can irritate the underlying skin and make the results of compression highly variable. Patient comfort and compliance is further reduced by the high profile or thickness and lack of thermal and/or moisture regulation of 3 to 4 layer systems, which can be difficult to wear under existing clothing or footwear and cause the uncomfortable buildup of body heat and moisture under the bandages.

Alternatively, other compression bandage systems have been proposed in attempts to counteract the complexities and time demands involved with the application of 3 to 4 layer bandage systems. For example, U.S. Pat. No. 7,854,716 discloses a two-part compression bandage system. The first part is an inner multi-layer elastic bandage comprising (1) an elastic substrate layer with a self-adhering outer face and an inner face affixed to (2) a foam layer having a skin-facing exposed face not affixed to the substrate layer. The second part of the system is a separate outer elastic layer with self-adhesion and compression properties. In application, the inner multi-layer bandage is wrapped around the patient's leg with the elastic substrate outer face configured and adapted to adhere to the separate outer elastic layer to prevent slippage or migration. Thus, the only purpose of the expensive elastic substrate layer of the inner bandage is to facilitate adhesion with the separate outer elastic layer. In addition to cost concerns, the two-part system falls short of optimizing patient comfort and, as a result, patient compliance with regard to its thickness, conformability, heat retention, and moisture regulation.

Moisture regulation in a compression bandage system is particularly important due to the seeping of serous fluid and other wound transudate and/or exudate from leg ulcers or other chronic wounds. Traditionally, cotton batting has been used under compression bandages for fluid absorption; however, the cotton often sticks to the affected area upon removal. Also of concern is the ability of any sub-bandage absorbent padding to remain compression neutral and minimize friction against the skin.

SUMMARY

In one aspect of the invention, a kit includes a first layer and a second layer. The first layer consists essentially of a foam material, and the second layer comprises an elastic material.

In another aspect of the invention, an article consists essentially of a foam layer having a first and second major surface. A hydrophilic coating is disposed on at least one of the first and second major surfaces.

In a further aspect of the invention, any of the foam layers and/or foam materials recited above have a length-to-width ratio between 20:1 to 100:1.

In yet another aspect of the invention, a method includes wrapping a first layer around a leg of a patient. The first layer consists essentially of a foam material. The method further includes wrapping a second layer around the leg of a patient. The second layer comprises an elastic layer and at least partially overlies the foam layer relative to the leg of the patient. Optionally, the foam material has a hydrophilic coating on a major surface.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

In general, embodiments of the invention provide a two-layer compression bandage system, including an inner layer, comprising a foam material, and an outer layer, comprising a separate elastic compression bandage. Some embodiments consist of only the inner foam layer having a hydrophilic coating on the skin-facing surface. Other embodiments may include one or more additional properties or layers, such as the separate elastic compression bandage, which can provide enhanced elasticity, durability, softness, and/or cohesion, as described below. Further embodiments provide for a compression bandage system that is partially or entirely latex free.

The choice of foam for the inner layer is useful in many respects. For example, the foam provides enhanced comfort and softness relative to non-foam bandages, and the pliability of the foam allows it to conform to most body parts without pleating or tucking, which can irritate the underlying skin and make the results of compression highly variable. Also, it has been observed that if the foam layer gets wet while it is wrapped around a body part, it does not unravel as conventional bandages would, but rather maintains the secure fit around the body part.

In addition, it is proposed that the microscopic structure of the foam enhances the cohesive properties of the foam layer. For example, the foam may include a plurality of open cells that have surfaces facing the exterior of the layer and appear to essentially form tiny, outward-facing "suction cups." If these suction cups are compressed against a surface, e.g., against another surface of the layer if the layer is wound around a body part, or against a non-porous surface of a medical device being affixed to a body part, the suction cups are believed to form a partial vacuum that imparts a particularly secure adhesive-like property to the layer.

It is also proposed that the inclusion of an irregular structure, such as a warp-knit weft-insertion fabric, in some embodiments of the separate elastic compression layer provides a rough surface to which the open cells of the foam will conform and form an even stronger interlocking mechanical interaction. Additionally, and unexpectedly, a degree of cohesive interaction is believed to exist in some embodiments in addition to the mechanical interaction that is obtained between the foam layer and a cohesive separate elastic compression layer. In some embodiments, it is proposed that the interactions between the two layers are further fortified by the cohesive properties within the overlays of both the foam layer and the separate elastic compression layer upon application.

It is proposed that the three forces detailed above result in a surprisingly robust interaction between the foam layer and the separate elastic compression layer, such that there is reduced slippage or migration between the layers following application. In fact, this has been confirmed by inspection of one embodiment of the two-layer compression bandage system following continuous all-day wear by human volunteers. Even when the system is removed from the leg by cutting straight across both layers, the foam layer and the separate elastic compression layer remain strongly joined. However, some other forces or interaction may be responsible for the connection between the foam layer and the separate elastic compression layer.

Compared to 3 to 4 layer compression bandage systems, the two-layer compression bandage system provides for greater patient comfort, which leads to increased compliance and better results. For example, in addition to avoiding pleats and tucks, the system allows for a low profile for ease of wear under existing clothing or footwear, reduced body heat retention in the patient's legs, and relatively smooth legs upon removal of the system when the layers are applied with 50% overlay.

In one implementation, the two-layer compression bandage system features a skin-facing hydrophilic surface. In certain embodiments, the hydrophilic surface is accomplished through the application of a hydrophilic agent to at least one surface of otherwise hydrophobic foam; however, in general, the hydrophilic agent need not be applied as long as at least one surface of the foam layer is hydrophilic. In another implementation consisting only of the foam layer, the skin-facing hydrophilic surface is achieved through the application of a hydrophilic agent.

The presence of the skin-facing hydrophilic surface is useful in many respects. For example, the application of the hydrophilic surface of the layer to the affected area of the patient's skin increases patient comfort by laterally wicking away serous fluid and other wound transudate and/or exudate while remaining compression neutral and keeping friction against the skin sufficiently low. In addition to keeping the skin dry and healthy, the combination of the foam structure and the skin-facing hydrophilic surface improves removal of the layer compared to traditional medical dressings like cotton batting; that is, the hydrophilic surface does not stick to the affected area at the time of removal to the degree seen in prior art systems.

Figure 1:
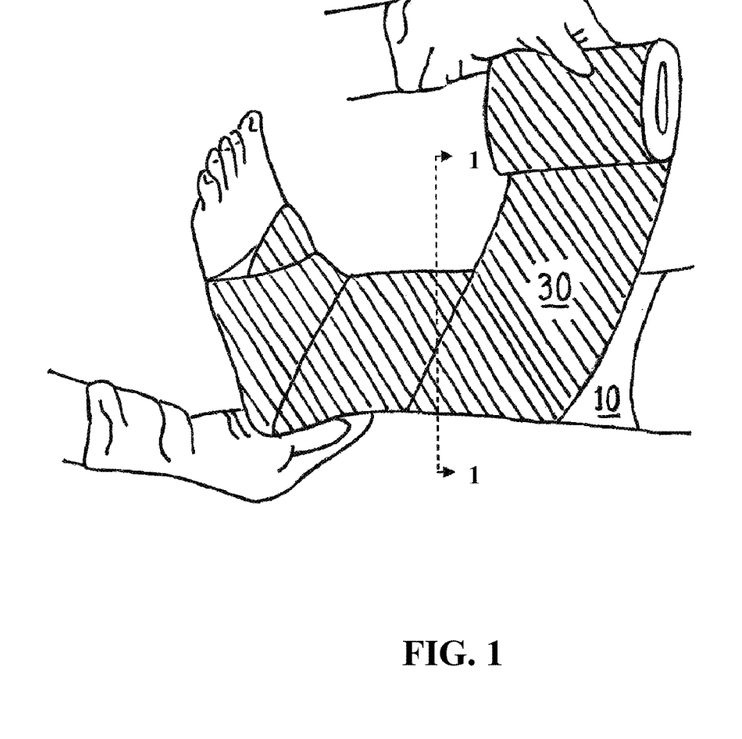
FIG. 1 is a depiction of a two-layer compression bandage system embodying the present invention.
Figure 2:
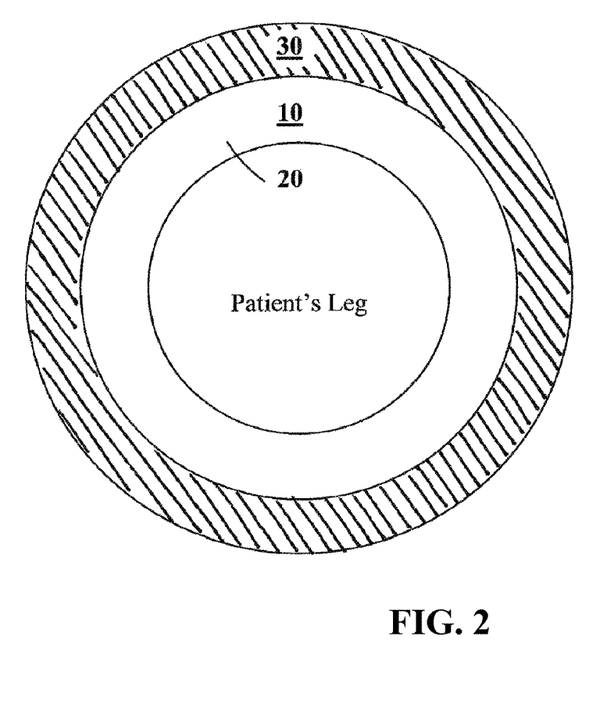
FIG. 2 is a cross-sectional view, taken at line 1-1 of the embodiment of FIG. 1, showing a separate outer elastic compression layer disposed on top of an inner foam layer according to one embodiment of the invention.
Figure 5:
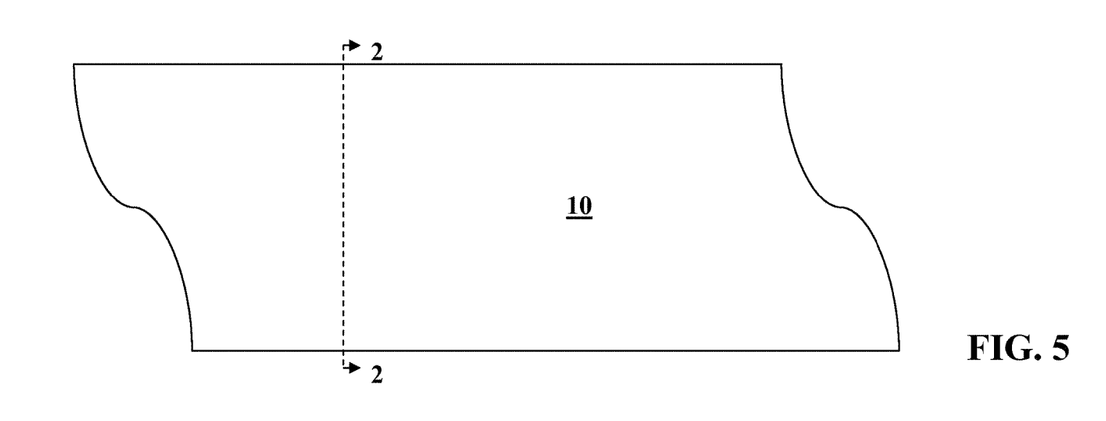
FIG. 5 is a top view of the foam layer according to one embodiment of the invention.
Figure 6:
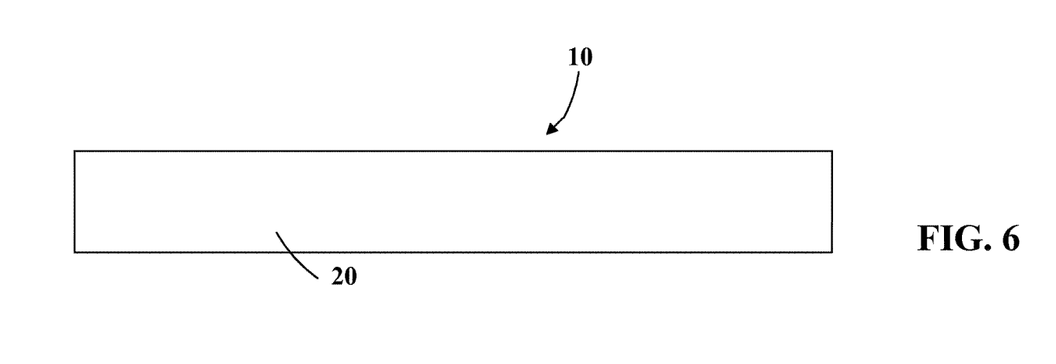
FIG. 6 is a cross-sectional view, taken at line 2-2 of the embodiment of FIG. 5, showing the skin-facing hydrophilic surface.
Figure 7:
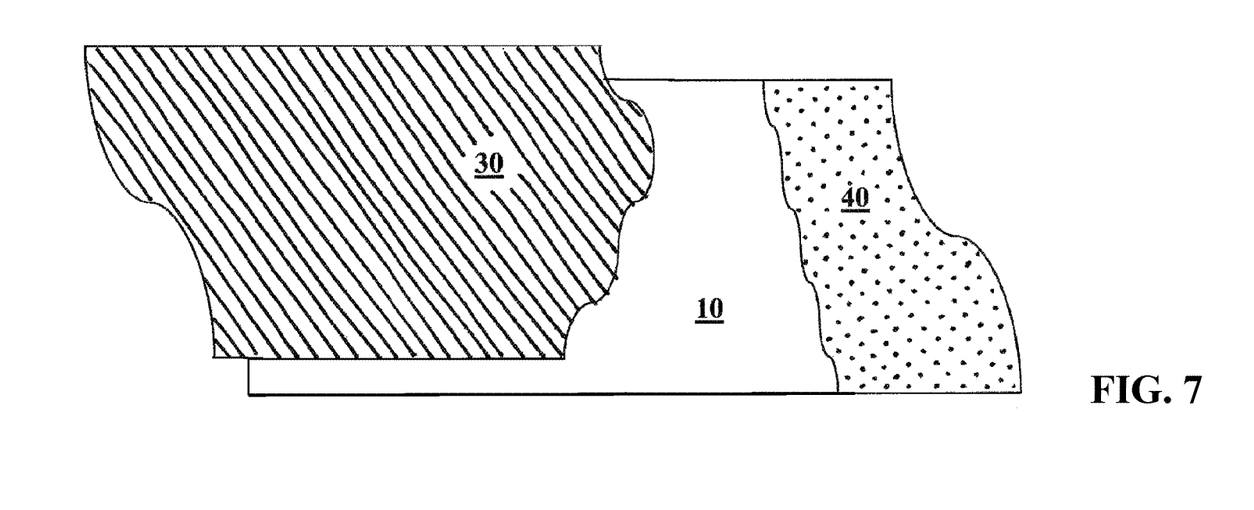
FIG. 7 is a top view, partially broken away, of the foam layer according to one embodiment of the invention.
Figure 8:
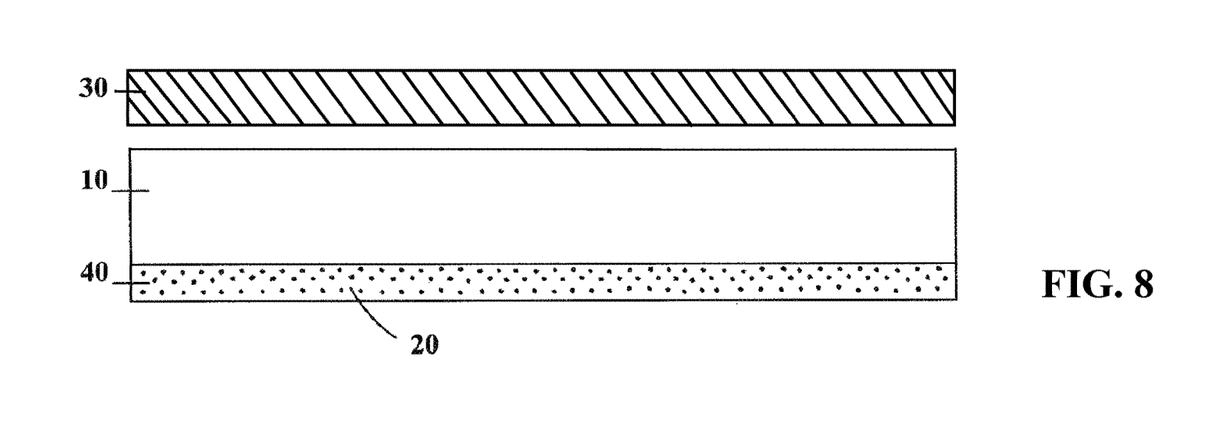
FIG. 8 is a cross-sectional view at line 3-3 of FIG. 7, showing the skin-facing hydrophilic surface of the foam layer and the separate elastic compression layer disposed on the opposite surface of the foam layer.

FIGS. 1 and 2 depict one illustrative embodiment of the two-layer compression bandage system, as wrapped around a patient's leg, comprising an inner foam layer, generally designated 10 and a separate elastic compression layer 30. In one implementation, the inner foam layer 10 has a skin-facing hydrophilic surface 20. Meanwhile, FIGS. 5 and 6 depict one illustrative embodiment of the foam layer 10 with the skin-facing hydrophilic surface 20. In addition, FIGS. 7 and 8 present another illustrative embodiment, in which a hydrophilic agent 40 has been applied to at least one surface of the foam layer 10 to achieve the skin-facing hydrophilic surface 20. Also in this embodiment, the separate elastic compression layer 30 has been disposed on top of the foam layer 10, opposite to the skin-facing surface, and secured in place by extraordinary cohesive-like interactions with the foam layer 10 and the secure winding of the separate elastic compression layer 30 upon itself around the patient's leg. In FIGS. 7 and 8, compression layer 30 is shown as spaced apart from foam layer 10 merely for the purposes of illustration. Upon application, it is understood that these layers will be in direct contact.

Although the embodiment of FIGS. 7 and 8 achieves the skin-facing hydrophilic surface 20 through the coating of hydrophobic foam with the hydrophilic agent 40, in general, a variety of different foams may be used in the foam layer 10, including a hydrophilic foam that makes it unnecessary to apply the hydrophilic agent 40 to a surface of the foam layer 10.

In use, foam is inherently elastic, that is, it can be deformed extensively and then substantially return to its original shape. Thus, the foam layer 10 can impart compression on a body part around which it is wound. However, in certain applications, the presence of the separate elastic compression layer 30 disposed on top of the foam layer 10, opposite to the skin surface, may enhance the compression the combination exerts if, for example, first the foam layer 10 and then the separate compression layer 30 are wound around a patient's leg.

As mentioned above, not all embodiments will include the hydrophilic coating 40 and/or the separate elastic compression layer 30, as the foam layer 10 itself may be made of hydrophobic or hydrophilic foam and still provide many useful properties, such as cohesion, softness, and durability.

Specific details of different kinds of useful foams, hydrophilic agents, and separate elastic compression layers can be found below.

The foam layer 10 with the skin-facing hydrophilic surface 20 may be wound into a roll. In some embodiments, the first major exterior surface of the foam layer 10 is wound onto and cohesively attaches to the second major exterior surface of the foam layer 10, or vice versa. In other embodiments, a removable release layer is placed in between major exterior surfaces of the foam layer 10. The release layer is not cohesive, but readily detaches from the major exterior surfaces of the foam layer 10. A release layer may be useful in circumstances where cohesion between the major exterior surfaces of the foam layer 10 is relatively high, and the presence of the release layer would facilitate unwinding of the rolled foam layer 10 or otherwise facilitate use of the foam layer 10. Note that the foam layer 10 need not be rolled in order to use a release layer.

Characteristics of Illustrative Embodiments of the Two-Layer Compression Bandage System In many embodiments, the foam layer 10 facing provides secure cohesive bonds, for example, when the foam front is bonded to the foam back, e.g., when the layer is wound upon itself to form front-to-back oriented layers, either on the roll or if it is used to wrap a body part. The strength of this secure cohesive bond between front-to-back oriented layers of the foam layer 10 can be characterized by a peel force bond strength of, for example, between about 6 kg/m-width (0.30 lb/in-width or piw) (5 oz/in-width) and 22 kg/m-width (1.25 piw) (20 oz/in-width), as measured in a standard peel force test performed following a standard application to patient, depending on the particular material properties, e.g., ratio of open cells to closed cells in the foam. In some embodiments, the peel bond force strength may be between about 2 kg/m-width (0.13 lb/in-width or piw) (2 oz/in-width) and 45 kg/m-width (2.50 piw) (40 oz/in-width), as measured in a standard peel force test performed following a standard application to patient.

In some embodiments, the secure cohesive bond provided by the foam layer 10 facing is further characterized by a shear force bond strength between about 3.4 kPa (0.5 psi) and 17.2 kPa (2.5 psi), as measured in a standard shear force strength test performed following a standard application to patient, depending on the particular material properties. In some embodiments, the shear force bond strength may be between about 0.7 kPa (0.1 lb/in$^2$ or psi) and 34.5 kPa (5.0 psi) in a standard shear force strength test performed following a standard application to patient.

In some embodiments, the foam layer 10 facing is characterized as "short stretch" due to its ability to stretch 30% to 45% beyond its original unstretched length. Unlike "long stretch" articles, which are able to stretch to several times or at least 100% beyond their original length and provide constant pressure at rest and work, i.e., a low static stiffness index (SSI), short stretch articles are able to provide more effective compression through a low resting pressure and a high standing pressure, i.e., a high SSI, greater than at least 10 mm Hg. The inherent elasticity of the foam determines, in part, the layer's ability to stretch. In some embodiments, the foam layer 10 may stretch between about 20% and 60%, or 10% and 90%, beyond its unstretched length. Also, certain short stretch embodiments of the foam layer 10 are designed to be applied at full stretch, thus reducing the variable compression effects of applying the layer to a body part under different conditions, e.g., application by different persons.

In some embodiments, the foam layer 10 facing may be further characterized by having a tensile strength of between about 21 kPa (3 lb/in$^2$ or psi) and 48 kPa (7 psi), for example about 34 kPa (5 psi), as measured in a standard tensile strength test.

In some embodiments, the foam layer 10 may be characterized by a length-to-width ratio of between about 20:1 and 100:1, depending on the type and size of the body part affected and the method of application.

Meanwhile, in some embodiments, the separate elastic compression layer 30 is disposed on top of the foam layer 10 and amounts to a separate layer that, in combination with the foam layer 10, provides suitable compression, abrasion protection, and/or security, e.g., reduced slippage, for use in applications such as, for example, wrapping a patient's leg or other body part or any other suitable application.

Like the foam layer 10, in preferred embodiments, the separate elastic compression layer 30 provides secure cohesive bonds to itself, for example, when the layer front is bonded to the back layer of the same material, e.g., when the layer is wound upon itself to form front-to-back oriented layers, either on the roll or if it is used to wrap a body part. Such embodiments eliminate the need for bandage clips or other fastening mechanisms.

Like the foam layer 10, in preferred embodiments, the separate elastic compression layer 30 is characterized as "short stretch" due to its inability to stretch more than 100% beyond its original unstretched length, thus leading to a high SSI. Also, certain short stretch embodiments of the separate elastic compression layer 30 are designed to be applied at full stretch, thus reducing the variable compression effects of applying the layer to a body part under different conditions.

In some embodiments, the separate elastic compression layer 30 may be characterized by a length-to-width ratio of between about 20:1 and 100:1, depending on the type and size of the body part affected and the method of application.

In further embodiments, the separate elastic compression layer 30 may amount to a separate layer that is latex free, as disclosed in U.S. Pat. No. 6,156,424, which is incorporated herein by reference in its entirety. In yet further embodiments, the separate elastic compression layer 30 may amount to a separate layer that eliminates the need for bandage scissors by facilitating hand-tearing, as disclosed in U.S. Pat. No. 5,762,623, incorporated herein by reference in its entirety. In still further embodiments, the separate elastic compression layer 30 may amount to a separate layer that provides extraordinary cohesive-like interaction with the foam layer 10 by comprising a warp-knit weft-insertion fabric, also disclosed in U.S. Pat. No. 5,762,623.

One suitable separate elastic compression layer that features all of the above advances is manufactured and sold by Andover Healthcare, Inc. (Salisbury, Mass.) under the trade designation "Co-Flex® NL." Co-Flex® NL is intended for controlled compression that will not constrict over time, i.e., a short-stretch bandage. In addition to its fabric-based dimensional stability and protection from dirt and moisture, Co-Flex® NL is porous, lightweight, and cohesive yet easy to remove.

Figure 9:
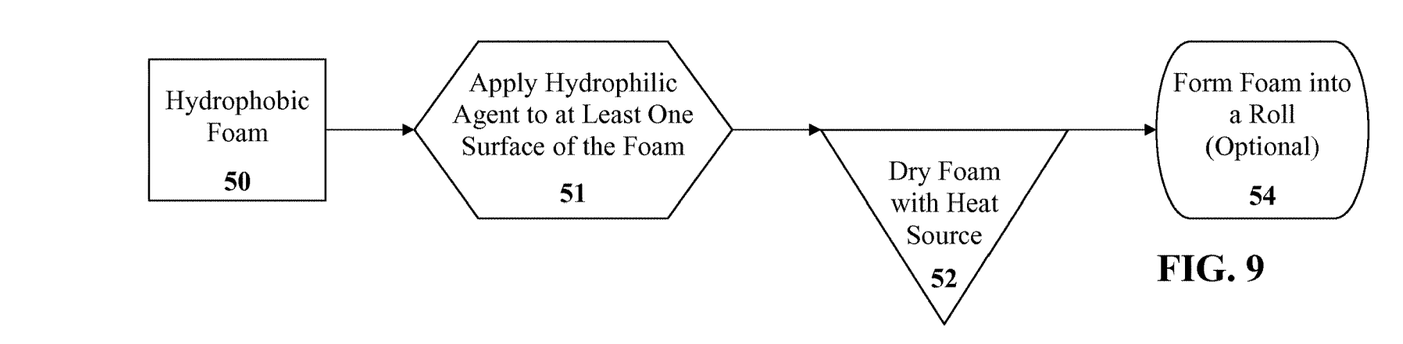
FIGS. 9 and 10 are flowcharts depicting processes for fabricating the foam layer with the skin-facing hydrophilic surface according to one or more embodiments of the invention.

Apparatus and Methods of Making the Foam Layer with the Skin-Facing Hydrophilic Surface A flowchart for preparing one embodiment of the foam layer with the skin-facing hydrophilic surface is shown in FIG. 9. In this embodiment, hydrophobic foam is provided 50 and coated on at least one surface with a hydrophilic agent 51. Then, the combination of the foam layer 10 and the skin-facing hydrophilic surface 20 undergoes a drying process 52, optionally with a heat source. Finally, the combination in this embodiment is formed into a roll 54. As in the flowchart shown in FIG. 10, if the foam provided is already hydrophilic 53, then the foam is formed into a roll 54, as in this embodiment, and either is used directly or rewound into a finished roll of any desired length, width, and winding tension.

Figure 11:
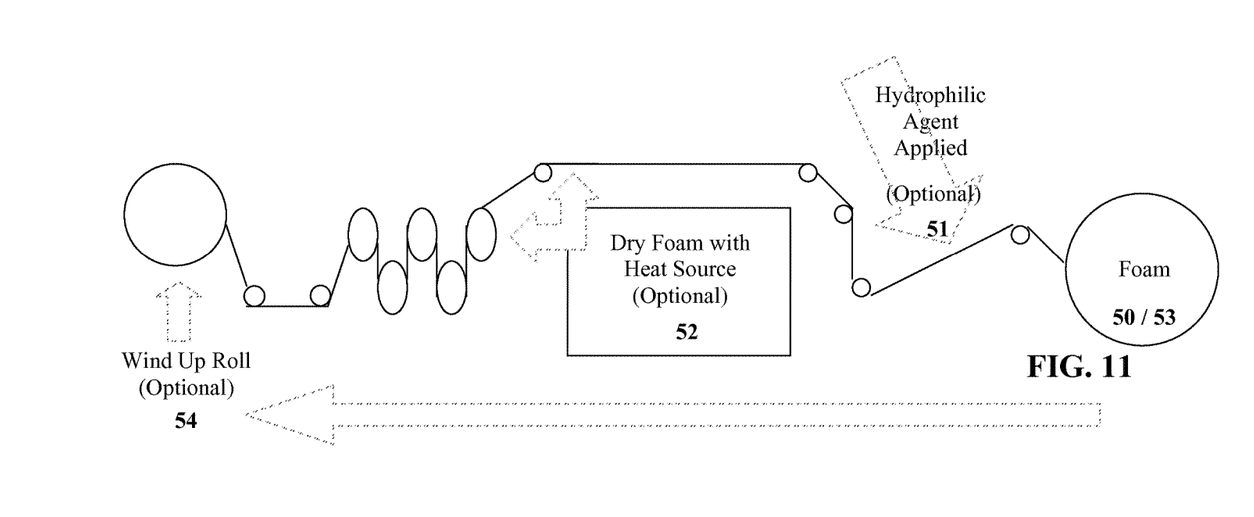
FIG. 11 is a depiction of an apparatus and process for fabricating the foam layer with the skin-facing hydrophilic surface according to one or more embodiments of the invention.

An illustrative apparatus for preparing one embodiment of the foam layer 10 with the skin-facing hydrophilic surface 20 is shown schematically in FIG. 11. The apparatus includes one feed roll for supplying foam, either hydrophobic 50 or hydrophilic 53. The foam is guided into nip rolls, which steady the foam while, in embodiments using the hydrophobic foam 50, a metered amount of the hydrophilic agent is applied to one major surface of the foam 51. As described in greater detail below, the hydrophilic agent can be, e.g., a vinyl acetate ethylene copolymer mixed with an antioxidant, a foaming agent, and a thickener. In these embodiments, the formulation is of a solids content and viscosity that permits coating of the foam. Although the actual composition may vary depending upon the particular foam, some illustrative formulations contain about 10% to 50% total solids and a viscosity of about 0.05 Pa·s to 0.5 Pa·s (50 cp·s to 500 cp·s) (Brookfield LV #3 at 30 rpm).

In certain embodiments, after passing through the nip rolls, the combination of the hydrophobic foam and the hydrophilic agent are dried by passing between an infrared heater and a heated plate maintained at an appropriate temperature 52. The heater can be heated air, heat lamps, or any other conventional source of heat. In addition, some embodiments may require the foam to be passed through multiple rollers to dry the foam. Then, in some embodiments, the finished product, whether hydrophilic foam or coated hydrophobic foam, is wound into a take-up roll 54. The take-up roll can then be used directly or rewound into a finished roll of any desired length, width, and winding tension.

Note that different embodiments of the foam layer 10 with the skin-facing hydrophilic surface 20 can be fabricated using modifications of the apparatus depicted in FIG. 11, or with entirely different machinery and/or methods. For example, if the foam already has a hydrophilic surface, those steps can be omitted.

Foam Layer

In some embodiments, the foam is a cellular sheet material formed of a suitable material, such as chemically foamed or aerated plastic material, foamed rubber or a non-hardening cellulose sponge material. In some embodiments, the foam includes a plurality of open cells which behave as tiny "suction cups" that enhance the cohesiveness of the layer. These open cells may define at least one of the major exterior surfaces of the layer. In some embodiments, the foam includes a plurality of closed cells. The closed cells do not necessarily provide as strong a "suction cup" effect as would open cells; however, the closed cells do provide enhanced cohesion and comfort relative to a foam-free product. The cohesion of the layer is adjusted by, among other things, selecting the ratio of open cells to closed cells in the foam.

Open cell foams and closed cell foams are well known in the art, and those of ordinary skill in the art will recognize that foams termed "open cell" will naturally include some closed cells, and that foams termed "closed cell" will naturally include some open cells. Thus the terms "open cell" and "closed cell" do not imply that the foam must necessarily include 100% open or 100% closed cells. In general, most of the cells are closed off from each other in closed-cell foams. Open-cell foams have an interconnecting cell structure, are generally softer than closed-cell foams, and have less structural integrity than closed-cell foams.

In some embodiments, the foam material includes one or more of polyurethane, polyester, polyester polyurethane, and polyethylene. The foam may have a weight of from about 75 g/cm$^2$ ($1.07 \times 10^{-4}$ lb/in$^2$) to 95 g/cm$^2$ ($1.35 \times 10^{-4}$ lb/in$^2$) or 45 g/m$^2$ ($0.61 \times 10^{-4}$ lb/in$^2$) to 125 g/m$^2$ ($1.82 \times 10^{-4}$ lb/in$^2$). In particular embodiments, the foam has a weight of about 85 g/m$^2$ ($1.21 \times 10^{-4}$ lb/in$^2$). When constructed of polyurethane, the foam generally has a density of about 23 kg/m$^3$ (1.5 lb/ft$^3$) to 29 kg/m$^3$ (1.9 lb/ft$^3$) or 13 kg/m$^3$ (0.9 lb/ft$^3$) to 39 kg/m$^3$ (2.6 lb/ft$^3$), e.g., about 26 kg/m$^3$ (1.7 lb/ft$^3$). The foam may have a thickness between about 0.15 cm (0.06 in) and 0.45 cm (0.18 in), for example, between about 0.27 cm (0.11 in) and 0.33 cm (0.13 in). The foam may be of any thickness desired for a particular application. In general, the greater the thickness, the greater the cushioning effect; however, a greater thickness also increases the bulk of the layer so the appropriate thickness will depend on the particular use. For example, thinner foam may be useful for leg wounds in which clothes would be worn over the wrapped layer, whereas thicker foam may be useful where applied over a bruise since it would provide more cushioning, or for use with animals in which case the wrapped layer would be likely to experience additional wear.

In some embodiments, the foam layer is a thin-gauge sheet of polyurethane or polyester polyurethane foam material having a thickness on the order of 0.30 cm (0.12 in). One suitable polyester polyurethane foam sheeting material type is manufactured and sold by William T. Burnett & Co. (Jessup, Md.) under the product identifier S82HD. This foam sheeting has a density of about 26 g/m$^3$ (1.7 lb/ft$^3$), a minimum tensile strength of 159 kPa (23 lb/in$^2$ or psi) and an average tensile strength of 207 kPa (30 psi), a minimum tear resistance of 525 N/m (3.00 lb/in-linear or ph) and an average tear resistance of 700 N/m (4.00 pli), and a minimum elongation of 300% and an average elongation of 450%, as determined by using the ASTM-D3574 standard methods of testing flexible cellular materials—slab, bonded, and molded urethane foam. The S82HD polyester polyurethane foam further has a minimum compression force of 2.8 kN/m$^2$ (0.40 psi) and an average compression force of 3.4 kN/m$^2$ (0.50 psi) at 25% deflection, and a minimum compression force of 3.1 kN/m$^2$ (0.45 psi) and an average compression force of 4.1 kN/m$^2$ (0.60 psi) at 50% deflection. The S82HD polyester polyurethane foam having a thickness of 0.3 cm (0.12 in) produces a layer with satisfactory cohesive and cushioning properties; however, other thicknesses, e.g., up to 0.5 cm (0.20 in) or even greater, may be employed to provide additional cushioning.

In some embodiments, the foam is fabricated or commercially purchased with a plurality of open cells on at least one of its major surfaces. At least some of the open cells remain open during fabrication of the layer. The open cells then act as "suction cups" and thus enhance the cohesiveness of the layer. In other embodiments, the foam is fabricated or purchased with a plurality of closed cells. In yet other embodiments, the foam is fabricated or purchased with an individual cell size that is maintained below a determined maximum, and a majority of the cells are of smaller size and extent than the size of the largest of the cells.

Hydrophilic Agent

In some embodiments where the foam layer 10 is hydrophobic, the skin-facing hydrophilic surface 20 is created through the application of a hydrophilic agent. The hydrophilic agent may be any formulation suitable for the absorption of serous fluid and other wound transudate and/or exudate while remaining compression neutral and keeping friction against the skin sufficiently low. In addition to providing for fluid drainage, the hydrophilic coating 40 improves removal of the layer compared to traditional medical dressings like cotton batting; that is, the skin-facing hydrophilic surface 20 does not stick as much to the affected area at the time of removal.

The amount of the hydrophilic coating 40 applied to the foam layer 10 may be between about 5 g/m$^2$ (0.10 oz/in$^2$) and 50 g/m$^2$ (0.91 oz/in$^2$), for example, between about 15 g/m$^2$ (0.27 oz/in$^2$) and 40 g/m$^2$ (0.73 oz/in$^2$). The hydrophilic coating 40 may be applied in any amount desired for a particular application. In general, the more coating, the greater the hydrophilic effect; however, more coating also increases the bulk and decreases the pliability of the foam layer 10 so the appropriate amount will depend on the particular use. For example, less coating may be useful for focused compression of a patient's leg, especially when clothes would be worn over the wrapped layer, whereas more coating may be useful where applied over a body part that is seeping serous fluid.

In some embodiments, the formulations for the hydrophilic coating 40 include a vinyl acetate ethylene (VAE). VAE is a copolymer of vinyl acetate and ethylene, ranging in content from 60% to 95% and 5% to 40% respectively. A higher ethylene concentration will result in increased flexibility and adhesion to low energy surfaces. VAE is available either as a water-based emulsion or in a powder form. The largest general areas of application for VAE are adhesives and sealants, which are generally intended to be water resistant. Thus, the inclusion of VAE in the formulation of an absorbent coating is a surprising characteristic of these hydrophilic agents. In some embodiments, the hydrophilic agent formulations include VAE mixed with an antioxidant, a foaming agent, and a prepared mixture of water and a thickener.

In some embodiments, the hydrophilic coating 40 is produced from acrylics, polyurethanes, and/or styrene butadiene.

Figure 12:
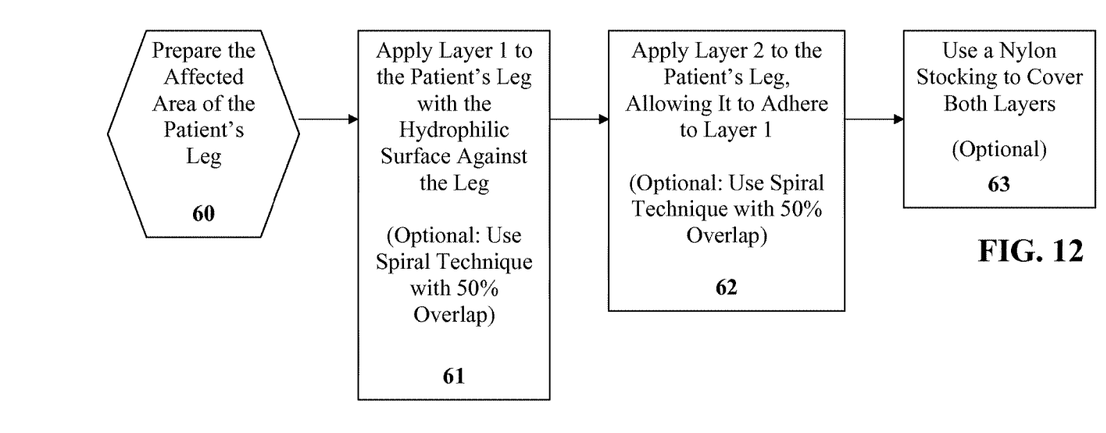
FIG. 12 is a flowchart depicting a method for using the two-layer compression bandage system with the skin-facing hydrophilic surface according to one or more embodiments of the invention.

Methods of Using the Two-Layer Compression Bandage System with the Skin-Facing Hydrophilic Surface An illustrative method for using one embodiment of the foam layer 10 with the skin-facing hydrophilic surface 20 is described by the flowchart in FIG. 12. First, the method involves cleaning and preparing the patient's leg for use of a bandage or wrap 60. Second, the foam layer 10 with the skin-facing hydrophilic surface 20, having been coated with the hydrophilic agent 40 for patient comfort and absorption in this embodiment, is applied directly to the patient's leg 61. A simple spiral wrapping technique and 50% overlap is one option here. Third, the separate elastic compression layer 30 is disposed directly on top of the foam layer 10, opposite to the skin surface 62. Again, a simple spiral wrapping technique and 50% overlap is one option. Fourth, optionally, a nylon stocking is used to cover the combined two-layer bandage system for a smooth outer surface that allows easy movement and may improve patient comfort 63.

Figure 3:
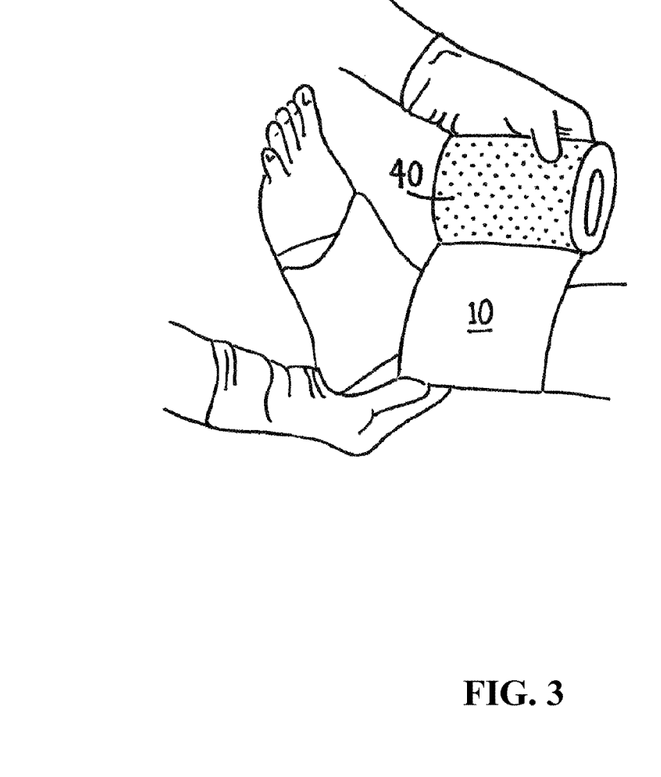
FIG. 3 is a depiction of a method for applying the foam layer to a patient's leg according to one or more embodiments of the invention.
Figure 4:
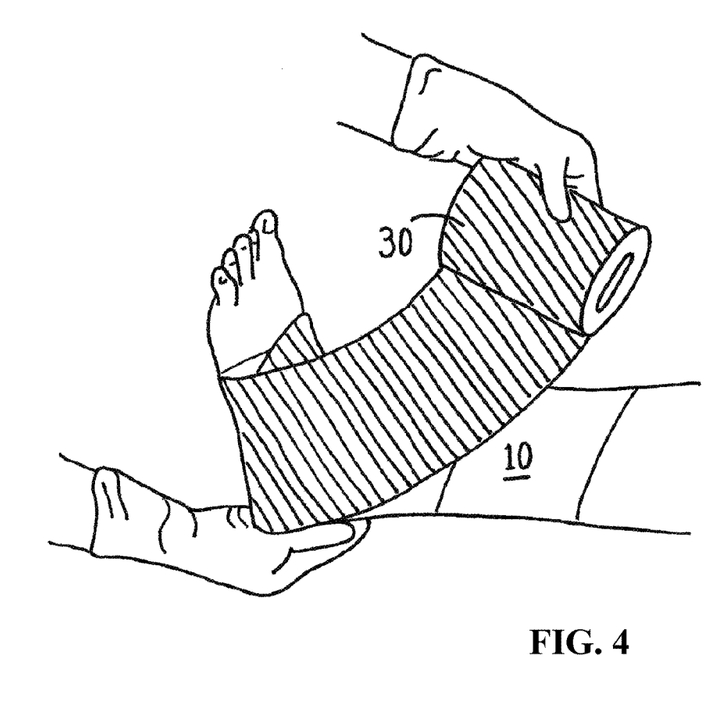
FIG. 4 is a depiction of a method for disposing the separate elastic compression layer on top of the foam layer according to one or more embodiments of the invention.

Likewise, in the illustrated embodiment shown in FIG. 3, the foam layer 10 with the skin-facing hydrophilic surface 20, having been coated with the hydrophilic agent 40 in this embodiment, is applied directly to the patient's skin and secured in place by winding the self-adhering foam layer 10 securely around the patient's leg. Also in this embodiment, and as shown in FIG. 4, the separate elastic compression layer 30 is disposed on top of the foam layer 10. The separate elastic compression layer 30 forms an extraordinary cohesive-like interaction with the foam layer 10, keeping the foam layer 10 secured in place. In some embodiments, the combination is further secured in place by securely winding the self-adhering compression layer 30 upon itself around the patient's leg.

Note that different embodiments of using the foam layer 10 with the skin-facing hydrophilic surface 20 can be designed using modifications of the method depicted in FIGS. 3-4 and 12, or with entirely different methods.

EXAMPLES

Various embodiments of the invention are further illustrated by the following examples, which should not be construed as limiting. In these illustrative examples, the construction of the foam layer with the skin-facing hydrophilic surface is described and its unique properties are tested. In addition, the construction and method of use of the illustrative foam layer with the separate elastic compression layer is described in detail.

Figure 10:
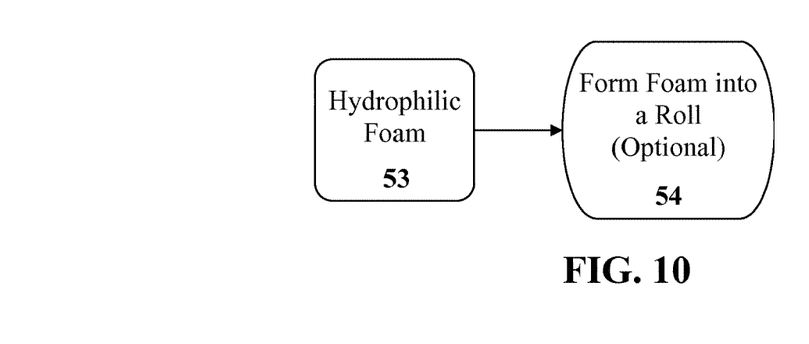

Construction of the Illustrative Foam Layer with the Skin-Facing Hydrophilic Surface The first illustrative foam layer 10 with the skin-facing hydrophilic surface 20 was constructed as shown in FIGS. 9-11, and described in further detail below. A thin layer of commercial polyester polyurethane foam 0.30 cm (0.12 in) thick (product S82HD from William T. Burnett & Co., Jessup, Md.) was provided. The foam layer has a density of about 26 g/m$^3$ (1.7 lb/ft$^3$), a minimum tensile strength of 159 kPa (23 lb/in$^2$ or psi) and an average tensile strength of 207 kPa (30 psi), a minimum tear resistance of 525 N/m (3.00 lb/in-linear or ph) and an average tear resistance of 700 N/m (4.00 pli), and a minimum elongation of 300% and an average elongation of 400%. The foam layer further has a minimum compression force of 2.8 kN/m$^2$ (0.40 psi) and an average compression force of 3.4 kN/m$^2$ (0.50 psi) at 25% deflection, and a minimum compression force of 3.1 kN/m$^2$ (0.45 psi) and an average compression force of 4.1 kN/m$^2$ (0.60 psi) at 50% deflection.

The foam was coated on one surface with 20 g/m$^2$ (0.37 oz/in$^2$) of a hydrophilic agent comprising a vinyl acetate ethylene (VAE) copolymer. To make the hydrophilic coating, 358.9 lbs. of a VAE copolymer dispersion (Vinnipas 405 from Wacker Polymers, Allentown, Pa.) was mixed with 3.9 lbs. of an antioxidant (Bostex 537 from Akron Dispersions, Akron, Ohio), 8.8 lbs. of a foaming agent (Unifroth 1672, from Unichem, Haw River, N.C.), and a prepared mixture of 20.7 lbs. of water and 7.7 lbs. of a polyacrylate thickener (Paragum 184 from Para-Chem, Dalton, Ga.). The resulting formulation weight was 400 lbs. Quality control evaluations required the range of total solids to be between 10% and 50%, the pH to be 4.0 to 8.0, and the viscosity to be 0.05 Pa·s to 0.5 Pa·s (50 cp·s to 500 cp·s) (Brookfield LV #3 at 30 rpm).

In some illustrative embodiments, the hydrophilic coating 40 comprises a VAE copolymer dispersion that is 75% Vinnipas 400 and 25% Vinnipas 405 or 75% Vinnipas 323 and 25% Vinnipas 405 (all available from Wacker Polymers, Allentown, Pa.).

Properties of the Illustrative Foam Layer with the Skin-Facing Hydrophilic Surface The first illustrative foam layer 10 (constructed with commercial polyester polyurethane S82HD from William T. Burnett & Co., Jessup, Md.) with the skin-facing hydrophilic surface 20 (coated with an agent comprising Vinnipas 405 from Wacker Polymers, Allentown, Pa.) provides secure cohesive bonds between its front-to-back oriented layers that can be characterized by a peel force bond strength of between about 6 kg/m-width (0.30 lb/in-width or piw) (5 oz in-width) and 22 kg/m-width (1.25 piw) (20 oz/in-width), as measured in a standard peel force test performed following a standard application to patient, and a shear force bond strength between about 3.4 kPa (0.5 lb/in$^2$ or psi) and 17.2 kPa (2.5 psi), as measured in a standard shear force strength test performed following a standard application to patient. This embodiment is characterized as "short stretch" due to its ability to stretch between about 30% and 45% beyond its unstretched length and by a tensile strength of about 34 kPa (5 psi), as measured in a standard tensile strength test.

In this embodiment, following the hydrophilic coating 40, the foam layer 10 has a minimum compression force of 2.8 kN/m$^2$ (0.40 psi) and an average compression force of 3.4 kN/m$^2$ (0.50 psi) at 25% deflection, and a minimum compression force of 3.1 kN/m$^2$ (0.45 psi) and an average compression force of 4.1 kN/m$^2$ (0.60 psi) at 50% deflection. The skin-facing hydrophilic surface 20 can be further characterized by a total absorption capacity of about 1800% and an absorption (wicking) rate of between 6 g (0.21 oz) of fluid per g (oz) of foam and 7 g (0.25 oz) of fluid per g (oz) of foam or, after 60 seconds of exposure to moisture, between 5 g (0.18 oz) of fluid per g (oz) of foam and 8 g (0.28 oz) of fluid per g (oz) of foam, as measured using the Gravimetric Absorption Testing System (M/K Systems, Inc., Peabody, Mass.).

Also in this embodiment, the average sub-bandage pressures were measured by the placement of 3 pressure transducers under this embodiment as wrapped around the legs of human volunteers. The average pressure measured at Transducer 1 at the ankle (leg circumference of 22 cm) was 21 mm Hg, the average pressure measured at Transducer 2 at mid-leg (leg circumference of 27 cm) was 22 mm Hg, and the average pressure measured at Transducer 3 at the calf (leg circumference of 33 cm) was 14 mm Hg.

Properties of the Two-Layer Compression Bandage System with the Skin-Facing Hydrophilic Surface The first illustrative foam layer 10 (constructed with commercial polyester polyurethane S82HD from William T. Burnett & Co., Jessup, Md.) with the skin-facing hydrophilic surface 20 (coated with an agent comprising Vinnipas 405 from Wacker Polymers, Allentown, Pa.) may be combined with the separate elastic compression layer 30 as shown in FIGS. 1-4 and 7-8, and described in further detail below. In this embodiment, the foam layer 10 is applied directly to the patient's leg and secured in place by winding the self-cohering foam layer 10 securely around the affected area. Also in this embodiment, and as shown in FIGS. 1 and 4, the separate elastic compression layer 30 (Co-Flex® NL, Andover Healthcare, Inc., Salisbury, Mass.) is disposed on top of the foam layer. With applications using patented Co-Flex® NL, it is proposed that the separate compression layer 30 mechanically interacts with the foam layer 10, keeping the foam layer 10 secured in place; the combination is further secured in place by winding the self-adhering elastic compression layer 30 upon itself around the patient's leg.

In this embodiment, the interaction between the foam layer 10 and the separate elastic compression layer 30 can be characterized by a peel force bond strength of between about 1.1 kg/m-width (0.06 lb/in-width or piw) (1 oz/in-width) and 22.3 kg/m-width (1.25 piw) (20 oz/in-width), as measured in a standard peel force test performed following a standard application to patient, and a shear force bond strength between about 3.5 kPa (0.5 lb/in$^2$ or psi) and 17 kPa (2.5 psi), as measured in a standard shear force strength test performed following a standard application to patient.

Also in this embodiment, the average sub-bandage pressures were measured by the placement of 3 pressure transducers under the combination in this embodiment, as wrapped around the legs of human volunteers. The average pressure measured at Transducer 1 at the ankle (leg circumference of 22 cm) was 42 mm Hg, the average pressure measured at Transducer 2 at mid-leg (leg circumference of 27 cm) was 51 mm Hg, and the average pressure measured at Transducer 3 at the calf (leg circumference of 33 cm) was 27 mm Hg.

Furthermore, the static stiffness index (SSI) of the combination in this embodiment was determined using a Pico-Press® Compression Measurement System according to the following method described in "The Static Stiffness Index: A Simple Method to Assess the Elastic Property of Compression Material in Vivo," H Partsch, Dermatol Surg, 31, 625-30 (2005). The resting pressure was 39 mm Hg, as measured at a defined position on the lower leg at rest, when the circumference at that position was minimal. The standing pressure was 63 mm Hg, as measured at the same position on the lower leg during active standing, when the circumference at that position had maximally increased due to muscle contraction. Thus, the SSI was 24 mm Hg, i.e., the difference between the standing pressure and the resting pressure.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

Having thus described the preferred embodiments, the invention is now claimed to be:

1. A compression bandage system for treating a body part, comprising:
   an inner, skin-contacting layer characterized by an elongate strip of a foam material, the foam material being pliable and having a first surface and a second surface opposite the first surface and a hydrophilic polymer coating disposed on the first surface, wherein the hydrophilic polymer coating is configured not to stick to the body part, the hydrophilic polymer coating comprising a mixture of a vinyl acetate ethylene (VAE) copolymer and a foaming agent, the first surface having the hydrophilic polymer coating configured to face and directly contact the body part during use, wherein said hydrophilic polymer coating does not extend substantially into the foam material, the inner, skin-contacting layer and the hydrophilic polymer coating configured to be wrapped circumferentially around the body part together and simultaneously; and
   a separate outer layer comprising an elastic, compression bandage, said separate outer layer configured to wrap separately from and around the inner, skin-contacting layer.

2. The compression bandage system of claim 1, wherein said foam material is selected from the group consisting of polyurethane foam, polyester foam, polyester polyurethane foam, and polyethylene foam.

3. The compression bandage system of claim 1, wherein said foam material is a hydrophobic foam material.

4. The compression bandage system of claim 1, wherein said compression bandage system does not include any additional layers.

5. The compression bandage system of claim 1, wherein said outer layer is a cohesive elastic bandage.

6. The compression bandage system of claim 5, wherein the inner, skin-contacting layer is self-adhering.

7. The compression bandage system of claim 5, wherein said outer layer has an irregular structure.

8. The compression bandage system of claim 7, wherein said outer layer comprises a warp-knit weft-insertion fabric.

9. The compression bandage system of claim 1, further comprising:
   said inner, skin-contacting layer stretchable to provide a compressive force when stretched, said inner, skin-contacting layer having an unstretched length and a maximum stretched length, wherein the maximum stretched length is not more than 100% greater than the unstretched length.

10. The compression bandage system of claim 1, further comprising:
    said outer layer stretchable to provide a compressive force when stretched, said outer layer having an unstretched length and a maximum stretched length, wherein the maximum stretched length is not more than 100% greater than the unstretched length.

11. The compression bandage system of claim 1, wherein the foam material has a thickness of about 0.15 cm to about 0.45 cm.

12. The compression bandage system of claim 1, wherein the hydrophilic polymer coating includes one or more additives selected from the group consisting of an antioxidant and a thickener.

13. The compression bandage system of claim 1, wherein the hydrophilic polymer coating is applied to the first surface in an amount ranging from 5 grams per square meter and 50 grams per square meter.

14. A method for applying a compression bandage system to a body part, said method comprising the steps of:
    providing an inner, skin-contacting layer characterized by an elongate strip of a foam material, the foam material being pliable and having a first surface and a second surface opposite the first surface and a hydrophilic polymer coating disposed on the first surface, wherein the hydrophilic polymer coating is configured not to stick to the body part, the hydrophilic polymer coating comprising a mixture of a vinyl acetate ethylene (VAE) copolymer and a foaming agent, the first surface having the hydrophilic polymer coating configured to face and directly contact the body part during use, wherein said hydrophilic polymer coating does not extend substantially into the foam material;
    circumferentially wrapping the inner, skin-contacting layer around the body part together and simultaneously with the hydrophilic polymer coating so that the first surface having the hydrophilic polymer coating directly contacts the body part; and
    circumferentially wrapping a separate outer, elastic, compression bandage layer around the inner, skin-contacting layer.

15. The method of claim 14, wherein said foam material is selected from the group consisting of polyurethane foam, polyester foam, polyester polyurethane foam, and polyethylene foam.

16. The method of claim 14, wherein said foam material is a hydrophobic foam material.

17. The method of claim 14, wherein said compression bandage system does not include any additional layers.

18. The method of claim 14, wherein said outer layer is a cohesive elastic bandage.

19. The method of claim 18, wherein the inner, skin-contacting layer is self-adhering.

20. The method of claim 18, wherein said outer layer has an irregular structure.

21. The method of claim 20, wherein said outer layer comprises a warp-knit weft-insertion fabric.

22. The method of claim 14, further comprising:
    said inner, skin-contacting layer stretchable to provide a compressive force when stretched, said inner, skin-contacting layer having an unstretched length and a maximum stretched length, wherein the maximum stretched length is not more than 100% greater than the unstretched length.

23. The method of claim 14, further comprising:
    said outer layer stretchable to provide a compressive force when stretched, said outer layer having an unstretched length and a maximum stretched length, wherein the maximum stretched length is not more than 100% greater than the unstretched length.

24. The method of claim 14, wherein the foam material has a thickness 0.15 cm to about 0.45 cm.

25. The method of claim 14, wherein the hydrophilic polymer coating includes one or more additives selected from the group consisting of an antioxidant and a thickener.

26. The method of claim 14, wherein the hydrophilic polymer coating is applied to the first surface in an amount ranging from 5 grams per square meter and 50 grams per square meter.

* * * * *